United States Patent
Ohtsuka

[11] 3,998,836
[45] Dec. 21, 1976

[54] KETIMINE DERIVATIVES AND PROCESS FOR PRODUCING THE SAME

[75] Inventor: Yozo Ohtsuka, Sagamihara, Japan

[73] Assignee: Sagami Chemical Research Center, Tokyo, Japan

[22] Filed: Aug. 12, 1974

[21] Appl. No.: 496,685

[30] Foreign Application Priority Data

Aug. 10, 1973 Japan .............................. 48-89326

[52] U.S. Cl. .................. 260/294.9; 260/240 K; 260/329 AM; 260/347.7; 260/465 E; 260/465.5 R; 71/81; 71/82; 71/83

[51] Int. Cl.² ............. C07D 273/84; C07D 307/66; C07D 333/36; C07C 121/20

[58] Field of Search ................ 260/465 E, 465.5 R, 260/294.9, 329 AM, 347.7, 240 K

[56] References Cited

UNITED STATES PATENTS

| | | | |
|---|---|---|---|
| 3,806,517 | 4/1974 | Begland | 260/465.5 R |
| 3,912,724 | 10/1975 | Begland | 260/465 E |
| 3,914,276 | 10/1975 | Begland | 260/465 E |
| 3,914,279 | 10/1975 | Begland | 260/465.5 R |

OTHER PUBLICATIONS

Robertson et al. J. Am. Chem. Soc. vol. 80 pp. 2691–2694 (1958).

Begland et al., in "J. Org. Chem." vol. 39, No. 16, (1974) pp. 2341 thru 2350.

*Primary Examiner*—Henry R. Jiles
*Assistant Examiner*—Robert T. Bond
*Attorney, Agent, or Firm*—Sughrue, Rothwell, Mion, Zinn & Macpeak

[57] ABSTRACT

Novel Schiff bases, ketimine derivatives, represented by the formula

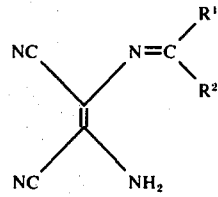

wherein $R^1$ and $R^2$ are as defined hereinafter, which possess a wide variety of utilities, and the process for producing the above ketimine derivatives from diaminomaleonitrile and a wide variety of aromatic α-ketones.

15 Claims, No Drawings

KETIMINE DERIVATIVES AND PROCESS FOR PRODUCING THE SAME

BACKGROUND OF THE INVENTION

1. Field of the Invention

This invention relates to novel Schiff bases, ketimine derivatives, represented by the formula

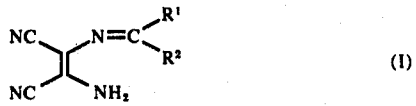

(I)

wherein $R^1$ represents a substituted or unsubstituted aromatic ring selected from the group consisting of phenyl, naphthyl, styryl and a heterocyclic group and $R^2$ represents an alkyl group having 1 to 8 carbon atoms or a substituted or unsubstituted aromatic ring selected from the group consisting of phenyl, naphthyl, styryl and a heterocyclic group, or $R^1$ and $R^2$ may form, when taken together with the carbon atom to which they are attached, a fluorenylidene or indenylidine group, the substituent on the aromatic ring being an alkyl group, a nitro group or a hydroxy group, and a process for producing the above ketimine derivatives which comprises reacting diaminomaleonitrile (hereinafter referred to as DAMN) with an aromatic α-ketone.

2. Description of the Prior Art

It was well known in the art that DAMN produces Schiff bases upon condensation with various aldehyde compounds or a specific ketone, i.e., d-camphor-10-sulfonate as described in M. P. Hartshorn and J. Vaughan, Chem. & Ind., 632 (1961). Also, it was known that certain pyrazine derivatives can be produced by condensation of DAMN with an α-diketone or an α-haloketone as described in E. Cyganeck, W. J. Linn and O. W. Webster, in "The Chemistry of the Cyano Group", ed. by Z. Rappoport, Interscience Publishing Co., London, 1970, p 508. However, the reaction between ketones and DAMN has not yet previously been reported.

In the conventional procedure, DAMM is reacted with a carbonyl compound by heating the reactants in the absence of solvents or in an alcohol solvent without using a catalyst, but it is said that no appreciable reaction occurs between a ketone compound and DAMN under such reaction conditions.

SUMMARY OF THE INVENTION

An object of this invention is to provide novel Schiff bases, i.e., ketimine compounds, represented by the formula I above which are useful as intermediates for the synthesis of a wide variety of organic compounds and which per se are useful as herbicides.

Another object of this invention is to provide a process for producing novel Schiff bases, ketimine compounds, of the formula I which comprises reacting DAMN with a ketone compound in the presence of a condensation agent.

DETAILED DESCRIPTION OF THE INVENTION

As a result of an extensive research, the present inventor found that a wide variety of aromatic α-ketones can be condensed with DAMN in the presence of a condensation agent as a catalyst under mild reaction conditions to produce the corresponding Schiff bases, i.e., ketimine compounds, in high yield.

The novel Schiff bases of the present invention can be represented by the formula

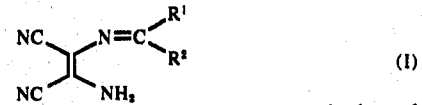

(I)

wherein $R^1$ represents a substituted or unsubstituted aromatic ring selected from the group consisting of phenyl, naphthyl, styryl and a heterocyclic group and $R^2$ represents an alkyl group having 1 to 8 carbon atoms or a substituted or unsubstituted aromatic ring selected from the group consisting of phenyl, naphthyl, styryl and a heterocyclic group, or $R^1$ and $R^2$ may form, when taken together with the carbon atom to which they are attached, a fluorenylidene or indenylidine group, the substituent on the aromatic ring being an alkyl group, a nitro group or a hydroxy group.

DAMN used in the present invention is a unique compound having a high nitrogen content which is easily available in industry. The ketone compounds used in the present invention are well known in the art and are generally used as solvents, intermediates for the organic synthesis of biologically active substances, etc., and most of the ketone compounds do not contain nitrogen atoms. In accordance with the process of this invention, a wide variety of compounds which would be useful in industry can be prepared by condensing DAMN and a ketone compound. For example, ketimine compounds of this invention are useful in the following utilities.

a. Agricultural agents such as herbicides.

b. Intermediates for the synthesis of heterocyclic compounds, and ketone-protective agents or reaction controlling agents in the synthesis of natural substances having ketone groups.

c. Synthesis of organic coloring materials.

These utilities are hereinafter described in greater detail.

Some of the Schiff bases of this invention exhibit heribicidal activities as shown in Reference Examples 1 to 4. Typical examples of the Schiff bases which are useful as a herbicide are 2-amino-3-[1-(p-nitrophenyl)ethylideneamino]maleonitrile and 2-amino-3-(9-fluorenylideneamino)maleonitrile.

Some of the Schiff bases of this invention produce hydrazones of the original ketones by treatment of the Schiff bases with a hydrochloric acid solution of 2,4-dinitrophenylhydrazine. Typical examples of the Schiff bases which are useful for the formation of hydrazones are 2-amino-3-(1-phenylethylideneamino)maleonitrile and 2-amino-3-diphenylmethyleneaminomaleonitrile which produce the corresponding hydrazone of the original ketone, i.e., acetophenone and benzophenone.

Some of the Schiff bases of this invention produce certain organic coloring materials. Such organic coloring materials can be produced by reacting a Schiff base with an aromatic carbonyl compound under basic conditions as illustrated in Reference Example 4. A typical example of the Schiff base which is useful for the formation of the organic coloring materials is 2-amino-3-diphenylmethyleneaminomaleonitrile.

The reaction between DAMM and an aromatic α-ketone in accordance with the process of this invention can be illustrated by the following embodiment where acetophenone is used as an aromatic α-ketone.

When DAMM is reacted with acetophenone in a molar ratio of about 1:1, the following Schiff base is produced through clevage of 1 mole of water.

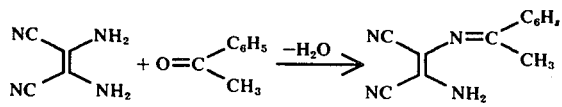

As set forth previously, the reaction of this invention proceeds through the condensation between 1 mole of an aromatic α-ketone and 1 mole of DAMN with the elimination of 1 mole of water. Therefore, the molar ratio of the ketone reactant and DAMN is advantageously used at least about 1 mole per 1 mole of DAMN. Any excess amount of ketone compounds does not adversely affect the reaction nor the product, and rather an excess of ketone compounds sometimes serves as a reaction solvent.

The condensation agents used as a catalyst can be those commonly employed as condensation agents in organic synthesis and include phosphoric anhydride (phosphorus pentoxide $P_2O_5$), concentrated sulfuric acid, dicyclohexylcarbodiimide, p-toluenesulfonic acid and the like. A particularly preferred dehydrating agent is phosphorus pentoxide. When phosphorus pentoxide is used, it can be used in an amount ranging from a catalytic amount (about 1/10 moles per 1 mole of DAMN) to an approximately equimolar amount relative to DAMN thereby providing approximately the same yield of the desired product. When phosphorus pentoxide is used in an amount lower than 1/10 mole, the reaction tends to require a prolonged period of time and, with higher amounts over the equimolar amount, the purity of the desired product tends to be lowered. A preferred amount of phosphorus pentoxide is about 1/3 mole per 1 mole of DAMN. However, it is to be understood that the optimum amount of phosphorus pentoxide and other condensation agents varies depending upon the type of ketone compounds as a reactant and is easily determined experimentally by those skilled in the art.

The reaction of this invention proceeds without using any solvents if the ketone compound is used in an excess amount over the amount required as a reactant. Also, the reaction of this invention can be conducted in the presence of an inert solvent such as an alcohol, for example, ethanol, chloroform and the like. The reaction can be conducted at a temperature of from about 0° C to about 100° C, preferably from room temperature (about 25° C) to about 80° C. Most of the reaction proceeds smoothly at room temperature and does not require heating or cooling, but if desired, the reaction system may be heated to accelerate the reaction.

After the reaction is completed, the precipitated product can be isolated from the reaction system by any conventional procedure such as filtration. When the desired product remains dissolved in the reaction mixture, the product can be isolated by concentrating the reaction mixture to remove the solvent and washing the resulting concentrate with water to remove the remaining catalyst and phosphoric acid produced from phosphorus pentoxide, if used as a catalyst.

The present invention is further illustrated by the following examples, but they are not to be construed as limiting the scope of this invention.

EXAMPLE 1

To a mixture of 3.0 g (0.028 moles) of DAMN and 8.3 g (0.069 moles) of acetophenone, 1.3 g (0.009 moles) of phosphorus pentoxide was added portionwise. The mixture was stirred for 1 hour at room temperature and then concentrated under reduced pressure. 20 ml of water was then added to the resulting residue, and the crystalline yellow solid thus obtained was separated by filtration. The crystals were then washed thoroughly with water and dried to obtain 4.3 g (74%) of the product as a yellow powder. For analysis, a sample of the product obtained above was repeatedly recrystallized from a mixture of isopropanol and acetone (3:1 by volume) to obtain a highly purified product as yellow needles having a melting point of 123° to 124° C. IR spectrum: 3450, 3280, 3130, 2235, 2200, 1600, 1574 and 1556. Mass spectrum: 210 (18, M$^+$), 196 (14), 195 (100), 168 (8), 141 (9), 133 (30) and 104 (14).

Analysis
Calcd. for $C_{12}H_{10}N_4$: C, 68.55; H, 4.79; N, 26.65
Found: C, 68.41; H, 4.84; N, 26.70

0.2 g of the above product was treated with 0.4 g of 2,4-dinitrophenylhydrazine solution in 70 ml of 2.6 N-HCl. After 2 hours stirring at room temperature, an orange precipitate (0.30 g) was collected and recrystallized from ethanol-ethyl acetate. This material (m.p. 249° – 251° C) was identified as 2,4-dinitrohydrazone of acetophenone by comparison with a sample prepared directly.

EXAMPLE 2

To a solution of 10.8 g (0.1 mole) of DAMN and 20.0 g (0.12 moles) of p-nitroacetophenone in 500 ml of ethanol, 4.0 g (0.03 moles) of phosphorus pentoxide was added portionwise. Yellow precipitates were obtained with a mild heat evolution which was removed by cooling with tap-water. After 15 minutes, the reaction mixture was cooled in an ice-bath and the product was then separated by filtration. The yield of the product was found to be almost quantitative. For analysis, a sample of the product obtained above was repeatedly recrystallized from an ethanol-acetone mixture (1:1 by volume) to obtain orange needles having a melting point of 221° – 222° C (after recrystallization from ethanol-acetone, 1:1 by volume). NMR spectrum: 2.59 (s, 3H, methyl protons), 8.27 (s, 4H, aromatic protons) and 7.70 (s, Ca.2H, amine protons). IR spectrum: 3430, 3310, 2220, 2170, 1594 and 1577. Mass spectrum: 372 (23, M$^+$), 345 (100), 344 (30), 330 (10), 304 (7), 239 (14), 225 (10) and 224 (8).

Analysis
Calcd. for $C_{12}H_9N_5O_2$: C, 56.47; H, 3.55; N, 27.44
Found: C, 56.74; H, 3.82; N, 27.44

EXAMPLE 3

2-Amino-3-[1-(o-Hydroxyphenyl)Ethylideneamino]-Maleonitrile

To a mixture of 3.0 g (0.028 moles) of DAMN, 3.8 g (0.028 moles) of o-acetylphenol and 60 ml of ethanol, 1.3 g (0.009 moles) of phosphorus pentoxide was added portionwise. The same treatment as described in Example 1 was followed to give yellow needles having a melting point of 181° – 183° C (after recrystallized from isopropyl alcohol). NMR spectrum: 2.51 (s, 3H, methyl protons) and 6.8 – 7.9. IR spectrum: 3400, 3290, 3180, 2225, 2180, 1621, 1598, 1546 and 1500. Mass spectrum: 226 (51, M$^+$), 212 (16), 211 (100), 199 (8), 183 (13), 171 (6), 132 (16), 119 (37) and 118 (14).

Analysis

Calcd. for $C_{12}H_{10}N_4O$: C, 63.70; H, 4.46; N, 24.77
Found: C, 63.76; H, 4.44; N, 24.70

EXAMPLES 4 to 11

Following the procedure described in Example 1, 2 or 3, various ketimine derivatives were produced from DAMN and a wide variety of ketone compounds. The reactants and the reaction conditions used in these examples as well as the results obtained are shown in Table 1 below.

EXAMPLE 4

2-Amino-3-Diphenylmethyleneaminomaleonitrile

This product was obtained from DAMN (10.8 g), benzophenone (19.0 g), $P_2O_5$ (4.0 g) and ethanol (200 ml) as yellow needles having a melting point of 168 – 169° C (after recrystallization from ethanol-water, 1:1 by volume). NMR spectrum: 7.2 – 7.8. IR spectrum: 3430, 3300, 2225, 2190, 1605, 1595, 1565 and 1550. Mass spectrum: 272 (20, M$^+$), 256 (5), 246 (2), 218 (15), 195 (100), 165 (29), 141 (13) and 115 (10).

Analysis

Calcd. for $C_{17}H_{12}N_4$: C, 74.98; H, 4.44; N, 20.58
Found: C, 75.00; H, 4.72; N, 20.28

0.276 g of the above product was treated with 0.4 g of 2,4-dinitrophenylhydrazine solution in 70 ml of 2.6 N-HCl. After 15 hours stirring at room temperature, a red precipitate (0.304 g, 82%) was collected and recrystallized from ethanol. This material (m.p. 245° – 246° C) was identified as 2,4-dinitrophenylhydrazone of benzophenone by comparison with a sample prepared directly.

EXAMPLE 5

2-Amino-3-[1-($\beta$-Naphthyl)Ethylideneamino]-Maleonitrile

This product was obtained from DAMN (3.0 g), 2-acetonaphthone (4.8 g), $P_2O_5$ (1.3 g) and ethanol (40 ml) as yellow needles having a melting point of 188° – 189° C (after recrystallized from ethanol). NMR spectrum: 2.65 (s, 3H, methyl protons) and 7.4 – 8.6. IR spectrum: 3400, 3250, 3100, 2210, 2180, 1587 and 1548. Mass spectrum: 260 (33, M$^+$), 259 (4), 246 (23), 245 (100), 243 (10), 234 (4) and 218 (4).

Analysis

Calcd. for $C_{16}H_{12}N_4$: C, 73.83; H, 4.65; N, 21.53
Found: C, 73.82; H, 4.57; N, 21.59

EXAMPLE 6

2-Amino-3-($\beta$-Naphthylphenylmethleneamino)-Maleonitrile

This product was obtained from DAMN (2.7 g), $\beta$-naphthyl phenyl ketone (5.8 g), $P_2O_5$ (1.3 g) and ethanol (100 ml) after extraction of an oily product with chloroform followed by crystallization of the concentrated extract from ethyl ethermethylcyclohexane as a yellow powder having a melting point of 180° –183° C (after recrystallization from ethanol-water, 5:1 by volume). NMR spectrum: 7.2 – 8.2. IR spectrum: 3450, 3330, 2220, 2180, 1582, 1567 (sh) and 1560 (sh). Mass spectrum: 322 (20, M$^+$321 (74), 320 (9), 306 (7), 305 (26), 295 (11), 293 (4), 270 (5), 269 (30) and 268 (100).

Analysis

Calcd. for $C_{21}H_{14}N_4$: C, 78.24; H, 4.38; N, 17.38
Found: C, 78.23; H, 4.26; N, 17.47

EXAMPLE 7

2-Amino-3-(9-Fluorenylideneamino)Maleonitrile

This product was obtained from DAMN (3.0 g), 9-fluorenone (6.0 g), $P_2O_5$ (1.3 g) and ethanol (100 ml) as red crystals having a melting point of 156° – 157° C (after recrystallization from benzene). NMR spectrum: 7.4 – 8.0. IR spectrum: 3400, 3280, 2235, 2190, 1610, 1595 and 1556. Mass spectrum: 270 (51, M$^+$), 269 (100), 268 (5), 243 (3), 216 (4), 215 (6), 191 (10), 190 (46), 189 (11) and 188 (11).

Analysis

Calcd. for $C_{17}H_{10}N_4$: C, 75.54; H, 3.73; N, 20.73
Found: C, 75.44; H, 3.46; N, 20.52

EXAMPLE 8

2-Amino-3-[1-(2-Thienyl)Ethylideneamino]-Maleonitrile

This product was obtained from DAMN (3.0 g), 2-acetylthiophene (3.6 g), $P_2O_5$ (1.3 g) and ethanol (80 ml) as yellow plates having a melting point of 177° – 179° C (after recrystallization from ethanol). NMR spectrum: 2.51 (s, 3H, methyl protons), 7.18 and 7.70 – 7.84 (t and m, respectively, total 3H, aryl protons) and 7.1 (broad peak, ca. 2H, amine protons). IR spectrum: 3430, 3310, 2220, 2180, 1583 and 1560 (sh). Mass spectrum: 216 (43, M$^+$), 203 (6), 202 (13), 201 (100), 174 (8), 147 (7), 133 (9), 110 (17) and 109 (24).

Analysis

Calcd. for $C_{10}H_8N_4S$: C, 55.55; H, 3.73; N, 25.92; S, 14.80
Found: C, 55.69; H, 3.94; N, 25.81; S, 14.70

EXAMPLE 9

2-Amino-3-[1-(2-Furyl)Ethylideneamino]-Maleonitrile

This product was obtained from DAMN (3.0 g), 2-acetylfuran (3.4g), $P_2O_5$ (1.4 g) and ethanol (30 ml) as yellow crystals having a melting point of 175° – 176° C (after recrystallization from ethanol). NMR spectrum: 2.43 (s, 3H, methyl protons), 6.80 (m, 1H, ring proton), 7.40 (t, 1H, ring proton), 7.93 (d-d, 1H, ring proton) and 7.25 (broad peak, ca. 1H, amine protons). IR spectrum: 3420, 3310, 3125, 2225, 2185, 1596, 1574 and 1552. Mass spectrum: 201 (7), 200 (50, M$^+$), 186 (16), 185 (100), 183 (6), 157 (21), 133 (8), 131 (5), 94 (11), 93 (13) and 66 (9).

Analysis

Calcd. for $C_{10}H_{18}N_4O$: C, 59.99; H, 4.03; N, 27.99
Found: C, 59.89; H, 3.76; N, 27.44

EXAMPLE 10

2-Amino-3-[1-(3-Pyridyl)Ethyleneamino]-Maleonitrile

This product was obtained from DAMN (3.0 g), 3-acetylpyridine (4.0 g), $P_2O_5$ (1.4 g) and ethanol (40 ml) as yellow crystals having a melting point of 230° – 232° C (after recrystallization from ethanol). NMR spectrum: 2.57 (s, 3H, methyl protons), 7.48 (q, ca.

2H, ring (5) + amine protons), 8.42 (d-t, 1H, ring (4) proton), 8.68 (d-d, 1H, ring (4) proton) and 9.23 (d, 1H, ring (1) proton). IR spectrum: 3400, 3230, ~ 2900 (broad), 2200 and 2170. Mass spectrum: 212 (5), 211 (30, M+), 197 (18), 196 (100), 169 (14), 142 (8), 133 (43), 105 (16), 104 (14), 179 (15), 178 (17) and 177 (7).

Analysis

Calcd. for $C_{11}H_9N_5$: C, 62.55; H, 4.30; N, 33.16
Found: C, 62.78; H, 4.20; N, 33.06

EXAMPLE 11

2-Amino-3-[(3-Pyridyl)Phenylmethyleneamino]-Maleonitrile

This product was obtained from DAMN (3.0 g), 3-benzoylpyridine (5.1 g), $P_2O_5$ (1.7 g) and ethanol (20 ml) as yellow crystals having a melting point of 217° - 218° C (dec.) (after recrystallization from ethanol). NMR spectrum: 2.47 (s, 3H, methyl protons), 7.3 – 8.0 and 8.5 – 8.9 (m, 9H, aryl protons). IR spectrum: 3360, 3225, 3030, 2220, 2180, 1623, 1602, 1593 and 1571. Mass spectrum: 274 (17), 273 (80, M+), 272 (7), 257 (7), 220 (14), 219 (24), 196 (87), 195 (100) and 166 (24).

Analysis

Calcd. for $C_{16}H_{11}N_5$: C, 70.32; H, 4.05; N, 25.62
Found: C, 70.16; H, 4.06; N, 25.41 spreading agents, wetting agents, stabilizers and the like, as well as fertilizers and other herbicides.

Typical examples of the ketimine derivatives which were found to be useful as herbicides are shown in Table II below:

Table II

| Compound No. | Chemical Structure |
| --- | --- |
| 1 | 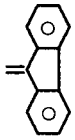 |
| 2 | 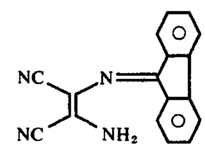 |

In investigating the herbicidal activity of the ketimine derivatives of this invention, the compounds listed in Table II above were tested as a wettable powder which was prepared by mixing and comminuting well a mixture comprising 10% by weight of each of the ketimine compounds to be tested, 85% by weight of talc (a filler available from Kukita Yakuhin Kogyo Co., Ltd., Ja- Table I Schiff Bases From DAMN And Ketones

| Example No. | Original Keytone | Reaction Conditions | | Yield (%) | R¹ | R² |
| --- | --- | --- | --- | --- | --- | --- |
| | | Time | Temperature | | | |
| 1 | MeCOPh | 1 hr | room temp. | 74 | $C_6H_5$ | $CH_3$ |
| 2 | MeCOPh-p-NO₂ | 10 mins | room temp. | 98 | p-NO₂—$C_6H_5$ | $CH_3$ |
| 3 | MeCOPh-o-OH | 46 hrs | room temp. | 34 | o-OH—$C_6H_5$ | $CH_3$ |
| 4 | PhCOPh | 4 hrs | room temp. | 93 | $C_6H_5$ | $C_6H_5$ |
| 5 | MeCONaph(β) | 30 mins | room temp. | 79 | —$C_{12}H_9$ | $CH_3$ |
| 6 | PhCONaph(β) | 37 hrs | reflux | 46 | —$C_{12}H_9$ | $C_6H_5$ |
| 7 | 9-Fluorenone | 2.5 hrs | reflux | 68 | | |
| 8 | MeCOTh(2) | 2 hrs | room temp. | 77 | 2-$C_4H_4S$ | $CH_3$ |
| 9 | MeCOFu(2) | 1 hr | room temp. | 73 | 2-$C_4H_4O$ | $CH_3$ |
| 10 | MeCOPy(3) | 1 hr | room temp. | 82 | 3-$C_5H_5N$ | $CH_3$ |
| 11 | PhCOPy(3) | 1 hr | reflux | 71 | 3-$C_5H_5N$ | $C_6H_4$ |

NOTE: Me: methyl, Ph: phenyl, Th: thenyl, Fu: furyl, Py: pyridyl

As set forth previously, the ketimine derivatives of this invention are useful for a wide variety of utilities. The following Reference Examples 1 to 3 illustrate the herbicidal activities of some of the ketimine derivatives of this invention, and Reference Example 4 illustrates the synthesis of a certain organic coloring agent from the ketimine derivatives of this invention.

The ketimine derivatives of this invention as herbicides are generally used as a wettable powder by combining at least one ketimine derivative as an active ingredient with appropriate fillers and surface active agent according to the technique well established in the art. They can be, of course, used in the form of emulsifiable concentrates, powders, dusts, granules or other preparations which are well known in the art by combining at least one ketimine compound with emulsifying agents, dispersing agents, suspending agents, pan) and 5% by weight of Neopelex Powder (a surface active agent available from Kao Soap Co., Ltd., Japan) using a triturator. The test methods and the results obtained are described below in greater detail.

Reference Example 1

Effect of Water Growing Phase Treatment

A paddy-field soil [diluvial volcanic soil (clay content, 37.5 – 50%)] was placed in a pot having a diameter of 9 cm (1/15500 acre), and 20 seeds of a barnyard grass were seeded uniformly on the surface of the soil. Two paddy-field rice plants at the three-leaf stage (Sasashigure species) were then planted at the center of the pot, and, at the same time, two additional rice plants of the same species as above were placed on the surface of the soil. Slender spikerush at an early growth stage was then planted around the rice plants and the soil was covered with water in a depth of 3 cm above the soil surface. The plants were then allowed to grow in a greenhouse. When the barnyard grass had grown to a 1.2 leafstage (about 2 to 3 cm in height), a predetermined amount of a wettable powder containing a ketimine derivative as an active ingredient was dissolved in 10 ml of water and added dropwise and uniformly to the water surface of the pot. In this experiment, N,N'-dichlorodiiminosuccinonitrile was also used as a control. The phytotoxic activities of each of the test compounds and the controls wer then observed on the 9th and 22nd days and the results are shown in Table III below according to the gradient between Normal Growth (0) and Complete Withering (5).

Table IV. In this example, N,N'-dichlorodiiminosuccinonitrile was used as a control. The phytotoxic effects observed on the 23rd day of the treatment are shown in Table IV, wherein the symbols "0" to "5" have the same meanings as defined in Reference Example 1.

Table IV

| Compound No. Tested | Concentration of Compound Applied (g/10 acres) | Rice Plant | Barnyard Grass | Mung-bean | Tomato Plant | Raddish | Crabgrass |
|---|---|---|---|---|---|---|---|
| 1 | 1000 | 0 | 0 | 0 | 0 | 0 | 0 |
| 2 | 1000 | 0 | 0 | 0 | 0 | 0 | 0 |
| N,N'-dichloro-diiminosuccino-nitrile | 300 | 0 | 0 | 0 | 0 | 0 | 0 |

Phytotoxic Effects of Soil Treatment in Field (on 23rd Day)

Reference Example 3

Effect of Stem and Leaf Treatment

The same soil as used in Reference Example 2 was seeded with various plant seeds in a similar manner to that described in Reference Example 2. After the seeded soil was covered with a soil, the seeds were allowed to germinate and grow to a 2.2 leaf stage in the Table III Effect of Submerged Treatment at Growing Stage (on 9th and 22nd Days)

| Compound No. Tested | Concentration of Compound Applied (g/10 acres) | 9th Day | | | | 22nd Day | | | | |
|---|---|---|---|---|---|---|---|---|---|---|
| | | Planted Rice Plant | Planted Rice Plant | Barnyard Grass | Slender Spike-rush | Planted Rice Plant | Planted Rice Plant | Barn-yard Grass | Slender Spike-rush | Broad Leaf Weeds |
| 1 | 2000 | 0 | 0 | 2 | 0 | 0 | 0 | 1 | 0 | Slightly developed |
| 2 | 2000 | 0 | 0 | 0 | 0 | 0 | 0 | 0 | 0 | Slightly developed |
| N,N'-dichlo-rodiimino-succinonitrile | 2000 | 0 | 0 | 0 | 0 | 0 | 0 | 0 | 0 | No development |

Reference Example 2

Effect of Soil Treatment in Field

A field soil [diluvial volcanic soil (clay content, 37.5 – 50%)] was placed into a series of the same pots as used in Reference Example 1 but having draining openings at the bottom, and the pots were seeded at equal intervals with various plant seeds indicated in Table IV below. The pots were then covered with the same field soil in a thickness of about 2 cm above the seeds. After water was thoroughly sprinkled on the seeded soil, an aqueous solution of a wettable powder containing each of the ketimine derivatives was applied uniformly to the soil surface of the pot in the concentration indicated in rice plant (Norin No. 24 species), a 2.5 leaf stage in the barnyard grass and crabgrass, a first leaf-development stage in mungbean, tomato plant and raddish. At this point, an aqueous solution of an emulsifiable concentrate containing each of the ketimine derivatives prepared by dissolving a predetermined amount of the ketimine derivative in 30 ml of water was sprayed well on the stem and leaves of the plants using a microsprayer. In this experiment, N,N'-dichlorodiiminosuccinonitrile was used as a control. The phytotoxic effects in each of the plants were observed on the 7th day of the treatment and the results obtained are shown in Table V below, wherein the symbols "0" to "5" have the same meanings as defined in Reference Example 1.

Table V

Phytotoxic Effects of Stem and Leaf Treatment (on 7th Day)

| Compound No. Tested | Concentration of Compound Applied (g/10 acres) | Rice Plant | Barnyard Grass | Mung-bean | Tomato Plant | Raddish | Crab-grass |
|---|---|---|---|---|---|---|---|
| 1 | 0.5 | 0 | 1 | 0 | 2 | 0 | 0 |
| 2 | 0.5 | 0 | 0 | 0 | 1 | 0 | 0 |
| N,N'-dichloro-diiminosuccino-nitrile | 0.5 | 0 | 2 | 0 | 1 | 0 | 0 |
| 1 | 1.0 | 0 | 2 | 0 | 4 | 3 | 0 |

Table V-continued

Phytotoxic Effects of Stem and Leaf Treatment (on 7th Day)

| Compound No. Tested | Concentration of Compound Applied (g/10 acres) | Rice Plant | Barnyard Grass | Mung-bean | Tomato Plant | Raddish | Crab-grass |
|---|---|---|---|---|---|---|---|
| 2 | 1.0 | 0 | 0 | 0 | 4 | 0.5 | 0 |
| N,N'-dichloro-diiminosuccino-nitrile | 1 | 0 | 3 | 4 | 2 | 3 | 1 |

Reference Example 4

A mixture of 3 g (0.01 mole) of 2-amino-3-diphenyl-methyleneaminomaleonitrile (product of Example 4) and 6 g (0.04 moles) of p-nitrobenzaldehyde in 20 ml of acetonitrile was cooled in ice-water and 1.6 g of triethylamine was added to the mixture. The mixture was stirred while cooling in icewater, and then kept over night in a refrigerator. The resulting precipitates were isolated by filtration to obtain orange fine powdery crystals in 70% yield. Recrystallization of the product thus obtained from acetonitrile gave orange crystals having a melting point of 211° to 213° C (decomposition).

Analysis

Calcd. for $C_{24}H_{17}N_5O_3$(1:1 adduct): C, 68,07; H, 4.05; N, 16.54
Found: C, 68.06; H, 4.26; N, 16.17
Mass spectrum: (150° C, 70eV) m/e = 422
NMR spectrum (in dimethyl sulfoxide-$d_6$) showed = 10.19 (aldehyde H) and the characteristic absorptions due to the starting material. From the above spectra, the product obtained above was proved to be a 1:1 adduct of 2-amino-3-diphenylmethyleneaminomaleonitrile and p-nitrobenzaldehyde. The product obtained by the procedure of Reference Example 4 was mixed with linseed oil and painted on test pieces, which were exposed to day-light for 3 months. These samples did not show any changes in their colors during the period of 3 months.

While the invention has been described in detail and with reference to specific embodiments thereof, it will be apparent to one skilled in the art that various changes and modifications can be made therein without departing from the spirit and scope thereof

What is claimed is:

1. A compound represented by the formula

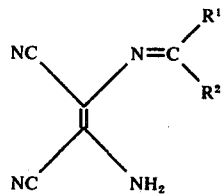

(I)

wherein $R^1$ represents a substituted or unsubstituted aromatic ring selected from the group consisting of phenyl, naphthyl, styryl and a heterocyclic group selected from the group consisting of thiophene, furan and pyridine and $R^2$ represents an alkyl group having 1 to 8 carbon atoms or a substituted or unsubstituted aromatic ring selected from the group consisting of phenyl, naphthyl, styryl and a heterocyclic group selected from the group consisting of thiophene, furan and pyridine, or $R^1$ and $R^2$ may form, when taken together with the carbon atom to which they are attached, a fluorenylidene or indenylidene group, said substituent on the aromatic ring being an alkyl group having 1 to 8 carbon atoms, a nitro group or a hydroxy group.

2. 2-Amino-3-(1-phenylethylideneamino)maleonitrile according to Claim 1.
3. 2-Amino-3-[1-(p-nitrophenyl)-ethylideneamino]-maleonitrile according to claim 1.
4. 2-Amino-3-[1-(O-hydroxyphenyl)-ethylideneamino]maleonitrile according to claim 1.
5. 2-Amino-3-diphenylmethyleneaminomaleonitrile according to claim 1.
6. 2-Amino-3-[1-($\beta$-naphthyl)-ethylideneamino]-maleonitrile according to claim 1.
7. 2-Amino-3-($\beta$-naphthylphenylmethyleneamino)-maleonitrile according to claim 1.
8. 2-Amino-3-(9-fluorenylideneamino)maleonitrile according to claim 1.
9. 2-Amino-3-[1-(2-thienyl)-ethylideneamino]-maleonitrile according to claim 1.
10. 2-Amino-3[1-(2-furyl)-ethylideneamino]-maleonitrile according to claim 1.
11. 2-Amino-3-[1-(3-pyridyl)-ethylideneamino]-maleonitrile according to claim 1.
12. 2-Amino-3-[(3-pyridyl)-phenylmethyleneamino]maleonitrile according to claim 1.
13. A process for producing a compound represented by the formula

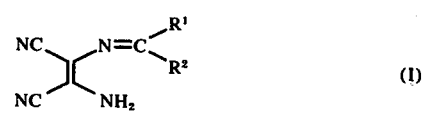

(I)

wherein $R^1$ represents a substituted or unsubstituted aromatic ring selected from the group consisting of phenyl, naphthyl, styryl and a heterocyclic group selected from the group consisting of thiophene, furan and pyridine, and $R^2$ represents an alkyl group having 1 to 8 carbon atoms or a substituted or unsubstituted aromatic ring selected from the group consisting of phenyl, naphthyl, styryl and a heterocyclic group selected from the group consisting of thiophene, furan and pyridine, or $R^1$ and $R^2$ may form, when taken together with the carbon atom to which they are attached, a fluorenylidene or indenylidene group, said substituent on the aromatic ring being an alkyl group having 1 to 8 carbon atoms, a nitro group or a hydroxy group, which comprises reacting diaminomaleonitrile with an aromatic α-ketone at a molar ratio of at least one mole of said aromatic α-ketone per one mole of diaminomaleonitrile at a temperature of from 0° to 100° C in the presence of a condensation agent selected from the group consisting of phosphoric anhydride, concentracted sulfuric acid, dicyclohexylcarbodiimide and a p-toluene-sulfonic acid.

14. The process according to claim 13, wherein said condensation agent is used in an amount of from 1/10 moles to 1 mole per 1 mole of diaminomaleonitrile.

15. The process according to claim 13, wherein said condensation agent is phosphorus pentoxide.

* * * * *